United States Patent
Sherer et al.

(10) Patent No.: US 9,314,376 B1
(45) Date of Patent: Apr. 19, 2016

(54) GOGGLES THAT ELIMINATE A USER'S PERIPHERAL VISION AND ENHANCE SITUATIONAL AWARENESS WHILE STRENGTHENING MUSCLE MEMORY

(71) Applicant: Swivel Vision, LLC, Orange, CA (US)

(72) Inventors: Ryan Calvin Sherer, Orange, CA (US); James Gerard Konkler, Orange, CA (US); Joseph James Valenti, Orange, CA (US)

(73) Assignee: Swivel Vision Sports LLC, Orange, CA (US)

( * ) Notice: Subject to any disclaimer, the term of this patent is extended or adjusted under 35 U.S.C. 154(b) by 0 days.

(21) Appl. No.: 13/622,225

(22) Filed: Sep. 18, 2012

Related U.S. Application Data

(60) Provisional application No. 61/541,746, filed on Sep. 30, 2011.

(51) Int. Cl.
   *A61F 9/02* (2006.01)
   *A63B 69/00* (2006.01)
   *A63B 69/36* (2006.01)

(52) U.S. Cl.
   CPC . *A61F 9/02* (2013.01); *A61F 9/029* (2013.01); *A63B 69/002* (2013.01); *A63B 69/36* (2013.01)

(58) Field of Classification Search
   CPC ......... A61F 9/02; A61F 9/029; A63B 69/002; A63B 69/36
   USPC ............. 2/12, 15, 431, 433, 439, 9, 202, 203, 2/205, 206, 423–425, 426; 351/53, 45; 473/458, 210
   See application file for complete search history.

(56) References Cited

U.S. PATENT DOCUMENTS

| | | | | |
|---|---|---|---|---|
| 2,694,263 A | * | 11/1954 | Francis et al. | 434/36 |
| 3,689,136 A | * | 9/1972 | Atamian | 351/44 |
| 4,059,347 A | * | 11/1977 | Eitel | 359/894 |
| 4,494,251 A | * | 1/1985 | Ainsworth et al. | 2/425 |
| 4,934,807 A | * | 6/1990 | Bolle et al. | 351/62 |
| 5,372,504 A | * | 12/1994 | Buechler | 434/35 |
| 5,661,534 A | * | 8/1997 | Gill | 351/41 |
| 6,141,797 A | * | 11/2000 | Buck | 2/15 |
| 6,390,619 B1 | * | 5/2002 | Gill, Jr. | 351/44 |
| 7,062,797 B2 | * | 6/2006 | Khulusi | 2/431 |
| 8,296,869 B2 | * | 10/2012 | Kellogg | 2/424 |
| 2009/0201466 A1 | * | 8/2009 | Knecht et al. | 351/206 |
| 2010/0259716 A1 | * | 10/2010 | Kusmec-Aguilar | 351/47 |

* cited by examiner

*Primary Examiner* — Katherine Moran
(74) *Attorney, Agent, or Firm* — Knobbe, Martens, Olson & Bear, LLP

(57) ABSTRACT

Goggles eliminate peripheral vision of a user and enhance situational awareness while increasing muscle memory. The goggles comprise a goggle frame mechanically coupled to a left side blinder and a right side blinder. The goggle frame is further mechanically coupled to a wearing component. The left side blinder covers approximately one half of a left eye of the user and the right side blinder covers approximately one half of a right eye of the user giving the user a field of vision of 30 degrees to 70 degrees which can eliminate distractions and disturbances in peripheral vision of the user causing increased situational awareness and increased muscle memory.

12 Claims, 3 Drawing Sheets

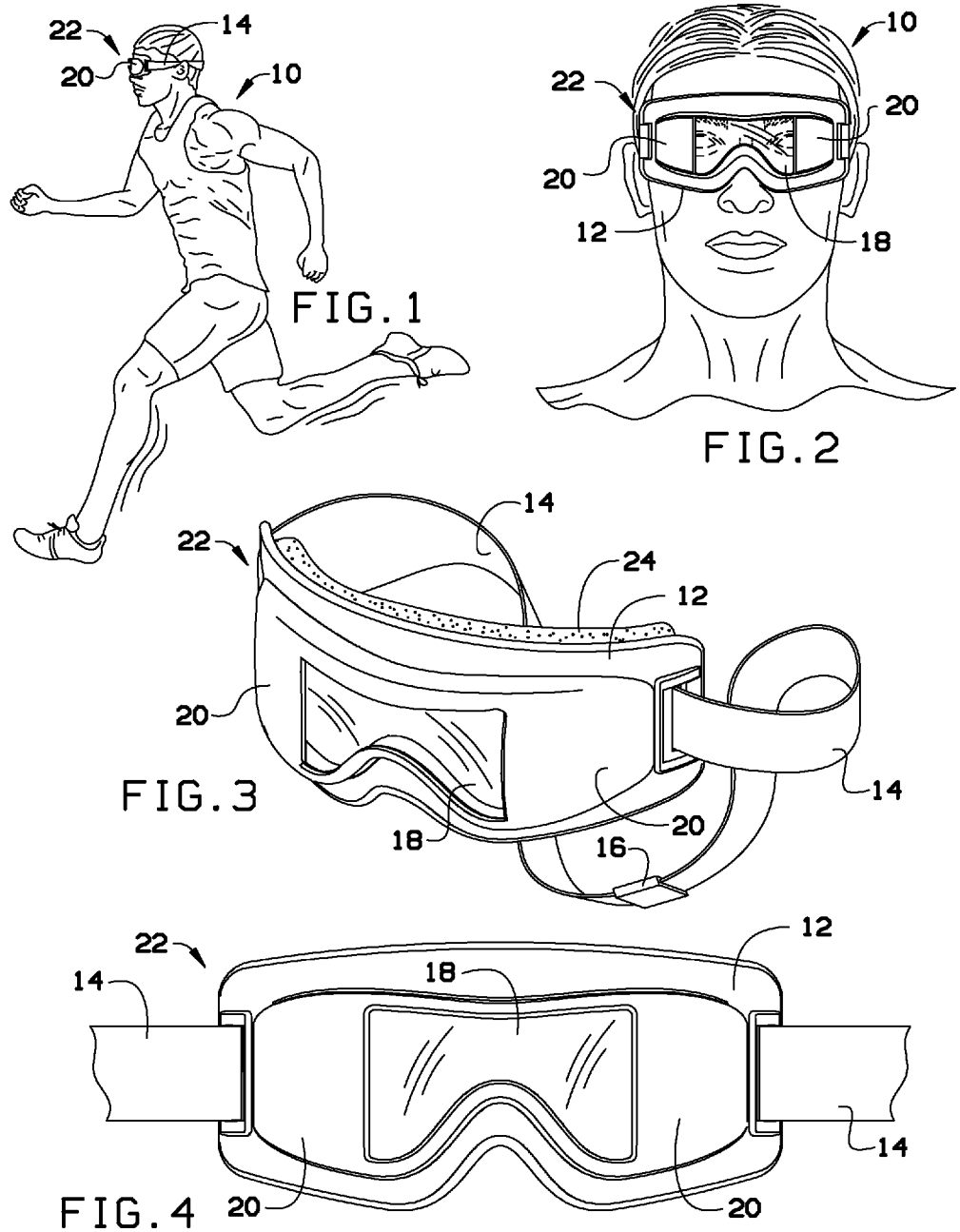

GOGGLES THAT ELIMINATE A USER'S PERIPHERAL VISION AND ENHANCE SITUATIONAL AWARENESS WHILE STRENGTHENING MUSCLE MEMORY

CROSS REFERENCE TO RELATED APPLICATIONS

This application claims priority to U.S. Provisional Application 61/541,746 filed on Sep. 30, 2011.

FIELD OF THE INVENTION

This invention relates to sports equipment, in particular sports equipment that is designed to strengthen core muscle memory.

BACKGROUND OF THE INVENTION

As used in this application "situational awareness" means the perception of environmental elements with respect to time and/or space, the comprehension of their meaning, and the projection of their status after some variable has changed, such as time. Situational awareness is reduced by disturbances or distractions in the environment.

As used in this application, "muscle memory" refers to both consolidating a specific motor task into memory through repetition along with the observation that various muscle-related tasks seem to be easier to perform after previous practice, even if the task has not been performed for a while.

Presently no sports equipment utilizes increased situational awareness to develop muscle memory like the present invention.

BRIEF SUMMARY OF THE INVENTION

The primary function of the disclosed goggle design is to enhance the athlete's peripheral vision. A typical athlete has a total field of vision ranging from 160 to 180 degrees. We achieve this by narrowing the athlete's field of vision to only one's optimal field of vision, which is approximately 30 to 70 degrees total. The goggles comprise a goggle frame mechanically coupled to a left side blinder and a right side blinder. The goggle frame is further mechanically coupled to a wearing component. When the goggles are removed after training, the athlete quickly recognizes an enhancement of peripheral vision. What makes the disclosed goggles unique and a must buy for athletes and coaches alike, is what happens while training with the goggle on: 1) promotes sound fundamental mechanics; 2) strengthens hand eye coordination while increasing focus; 3) quickens reaction time; 4) enhances situational awareness The disclosed goggles force the athlete to keep their head on a swivel and square to the object of interest with an increased focus. Any deviation of site away from object will result in the athlete not seeing object. This allows the athlete to correct themselves and begin to follow the object all the way to the point of contact. Building solid fundamental mechanics based on proper technique and positive muscle memory over time if worn on a continual basis during training.

BRIEF DESCRIPTION OF THE SEVERAL VIEWS OF THE DRAWINGS

Figure 5:
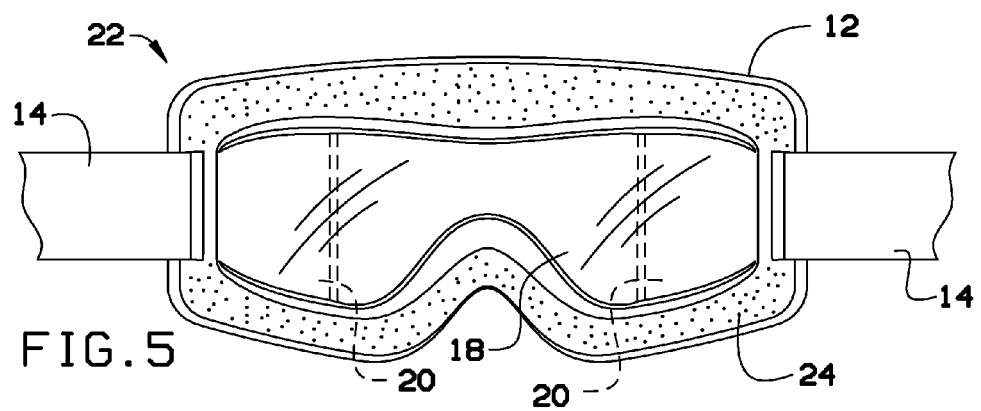
Figure 6:
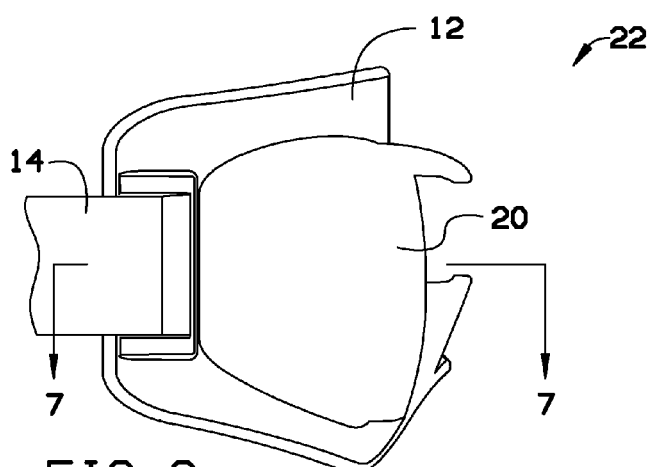
Figure 7:
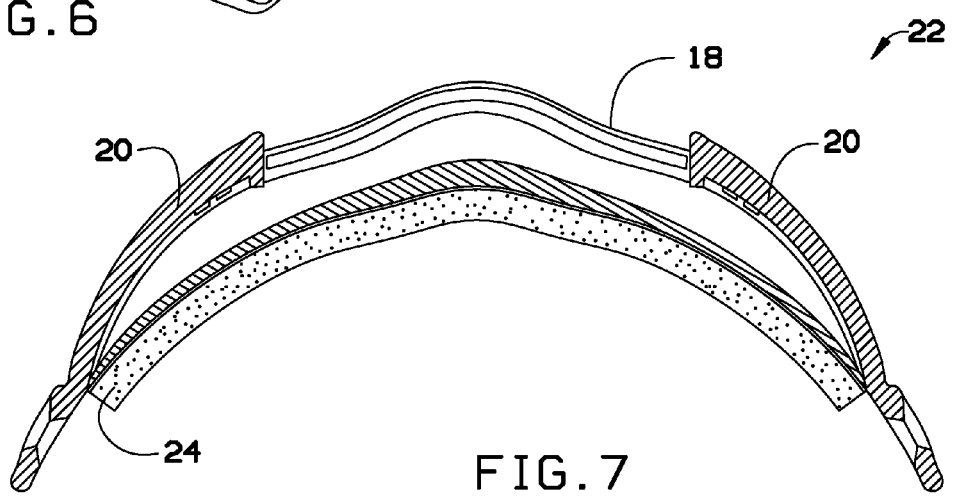
Figure 8:
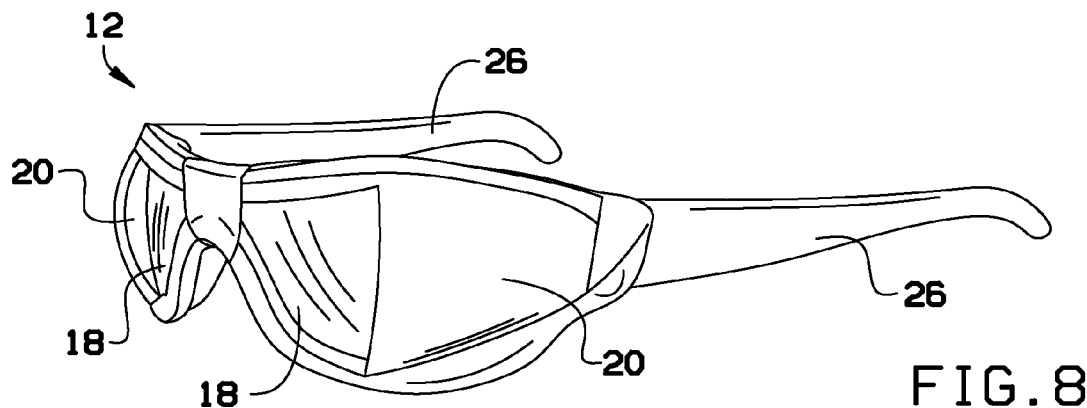
Figure 9:
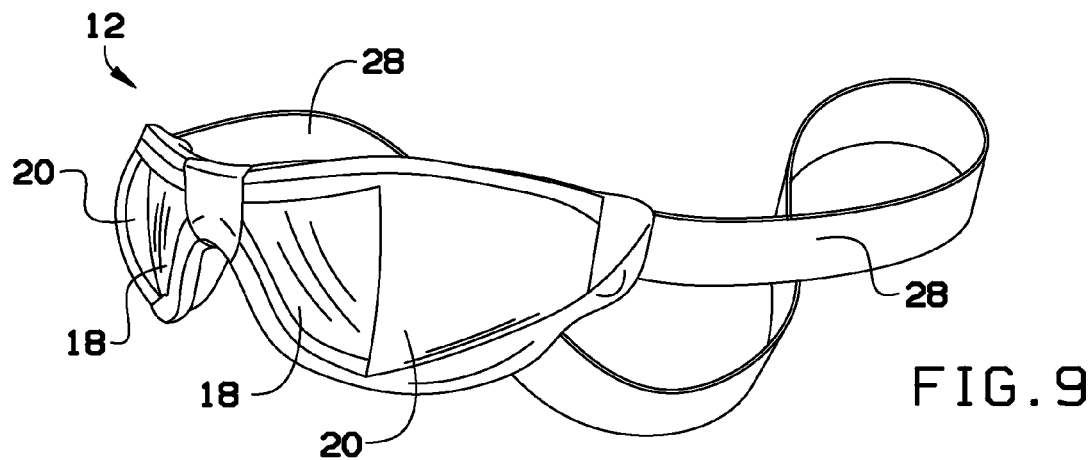

Having thus described the invention in general terms, reference will now be made to the accompanying drawings, which are not necessarily drawn to scale, and wherein:

FIG. 1 is a side view of the invention shown in use.
FIG. 2 is a forward view of the invention shown in use.
FIG. 3 is a perspective view of the invention.
FIG. 4 is a forward view of the invention.
FIG. 5 is a rear view of the invention.
FIG. 6 is a side view of the invention.
FIG. 7 is a section detail view of the invention along line 7-7 in FIG. 6.
FIG. 8 is a perspective view of an alternate embodiment of the invention with removable arms.
FIG. 9 is a perspective view of an alternate embodiment of the invention with a removable strap.

DETAILED DESCRIPTION OF THE INVENTION

Embodiments of the present invention overcome many of the obstacles associated with utilizing increased situational awareness to develop muscle memory, and now will be described more fully hereinafter with reference to the accompanying drawings that show some, but not all embodiments of the claimed inventions. Indeed, the invention may be embodied in many different forms and should not be construed as limited to the embodiments set forth herein. Rather, these embodiments are provided so that this disclosure will satisfy applicable legal requirements. Like numbers refer to like elements throughout.

FIG. 1 shows the invention in use. User 10 desires to develop muscle memory by increasing situational awareness. User 10 can do this by wearing goggles 22 with strapping 14. Goggles 22 comprise side blinders 20 as shown in more detail in FIG. 2.

FIG. 2 shows a front perspective view of user 10 wearing goggles 22. Goggle frame 12 is mechanically coupled to left side blinder 20, front window 18 and right side blinder 20. In the preferred embodiment, goggles 22 are custom made such that right side blinder 20 is aligned to cover approximately half of a right eye of user 10. Likewise, left side blinder 20 is aligned to cover approximately half of a left eye of user 10. In this manner, user 10 has a field of vision through front window 18 of approximately 30 degrees to 70 degrees. This is the preferred field vision in order to reduce distractions and disturbances and thus increase situational awareness. The reduced distractions and disturbances also allow for repetitive motion to increase muscle memory.

FIG. 3, FIG. 4 and FIG. 5, FIG. 6 and FIG. 7 show goggles 22 in more detail.

Goggles 22 comprise goggle frame 12 mechanically coupled to left side blinder 20, right side blinder 20 and window 18. In some embodiments, right side blinder 20 and left side blinder 20 are formed into a single unit around window 18. Goggles 12 are further mechanically coupled to padding 24 and strapping 14. Strapping 14 can be adjusted by adjusting couple 16.

While goggles 22 can be made of a variety of materials in a variety of known methods, in the preferred embodiments goggle frame 12 can be made with plastic injection molding in a single unit with side blinders 20. As shown in FIG. 6, side blinders 20 can have an overhang over front window 18 that can prevent distractions from above the user from reducing situational awareness.

Front window 18 can either be made of a transparent plastic, glass, or front window 18 can simply be open to the external environment. When made of a transparent plastic or glass front window 18 can protect the eyes of user 10 from external debris. Goggle frame 12 can be affixed to padding 24 with a known adhesive. For example, if padding 18 is made of foam, goggle frame 12 can be glued to the foam. Regardless of material, padding 18 cushions goggle frame 12 against a head of the user. Strapping 14 can be nylon with elastic strapping. Strapping 14 is one wearing component that can be use and alternatives are shown in FIG. 8 and FIG. 9.

FIG. 8 shows an alternate embodiment where the wearing component is removable arms 26. Removable arms 26 can be affixed to goggle frame 12 with screws in a manner commonly used by glasses.

FIG. 9 shows an alternate embodiment where the wearing component is removable strap 28. While similar in function and material to strapping 14, removable strap 28 can be made of a rubber material and attached to goggle frame 12 in a manner similar to swimming goggles.

There are many uses for goggles 22 to reduce distractions and disturbances, because the user cannot see them, and thus increase situational awareness and muscle memory. As a non-exhaustive list of examples:

In taking test, students will be more focused on the exam by eliminating other distractions that may sway their attention. Further, goggles 22 can reduce cheating because the student would have to turn their heads fully and expose their intent.

For students with attention deficit disorder (ADD) and similar conditions, goggles 22 can eliminate distractions seen through peripheral and reasons to derail the attention of students who suffer with ADD. By eliminating as many potential distractions to ADD students a user can increase the student's attention span.

For training racecar drivers and other racing sports goggles 22 require the driver to focus on what is ahead and increase the driver's speed. However, goggles 22 are designed to be used when the driver is solo on track for training.

In sports that have many peripheral distractions and disturbances such as surfing, skateboarding, wakeboarding, snowboarding and any other board sport goggles 22 can reduce the disturbance or distraction for user 10.

Law enforcement and military personnel may use goggles 22 in their training to enter buildings with a firearm drawn to help with focus on a correct target.

The invention claimed is:

1. Goggles configured to eliminate peripheral vision of a user and enhance situational awareness while increasing muscle memory, the goggles comprising:
   a goggle frame shaped to extend around eyes of a user, extending in a horizontal direction between left and right portions and extending vertically between upper and lower portions, the goggle frame supporting a left side blinder and a right side blinder;
   the left side blinder extending from the left portion toward the right portion and terminating at a vertical edge positioned so as to be aligned approximately with a center of a user's left eye when worn by the user and to thereby obscure approximately a left visual hemifield of the left eye, the vertical edge of the left side blinder comprising a left rib extending from the upper portion to the lower portion and extending inwardly from an outer surface past an inner surface of the left side blinder to thereby increase mechanical rigidity of the left side blinder;
   the right side blinder extending from the right portion toward the left portion and terminating at a vertical edge positioned so as to be aligned approximately with a center of a user's right eye when worn by the user and thereby obscure approximately a right visual hemifield of the right eye, the vertical edge of the right side blinder comprising a right rib extending from the upper portion to the lower portion and extending inwardly from an outer surface past an inner surface of the right side blinder to thereby increase mechanical rigidity of the right side blinder;
   where the goggle frame is further mechanically coupled to a wearing component;
   wherein the goggles do not have any visual obstruction in a central area of the goggles between the left and right vertical edges and between the upper and lower portions, giving the user an unobstructed binocular field of vision through the central area of the goggles.

2. The goggles of claim 1, wherein the right side blinder and the left side blinder are formed into a single unit around the central portion with an overhang over the central portion that can prevent distractions from above the user from reducing situational awareness.

3. The goggles of claim 1, additionally comprising a wearing component comprising strapping, which can be adjusted with an adjusting couple.

4. The goggles of claim 1, additionally comprising a wearing component comprising removable arms, which can be used in a manner similar to glasses.

5. The goggles of claim 1, additionally comprising a wearing component comprising adjustable strapping, which can be used in a manner similar to swimming goggles.

6. The goggles of claim 1, further comprising a boundary member extending along a periphery of the goggle frame.

7. The goggles of claim 6, wherein the boundary member is configured to be pressed against a head of a user along a portion of a user extending around eyes of the user.

8. The goggles of claim 7, wherein the boundary member is compressible.

9. The goggles of claim 6, wherein the boundary member comprises foam padding configured to cushion the goggle frame against a head of the user.

10. The goggles of claim 1, wherein the goggle frame comprises removable arms.

11. The goggles of claim 10, wherein the wearing component comprises adjustable strapping.

12. The goggles of claim 10, wherein the left and right vertical edges are spaced so as to provide a user with an unobstructed field of vision of about 30 degrees to 70 degrees measured in the horizontal direction.

\* \* \* \* \*